US010586022B2

(12) United States Patent
Czaplewski et al.

(10) Patent No.: US 10,586,022 B2
(45) Date of Patent: Mar. 10, 2020

(54) SYSTEM AND METHOD FOR MANAGING INVENTORY AT DISPENSING UNITS

(71) Applicant: OMNICELL, Inc., Mountain View, CA (US)

(72) Inventors: Jason Czaplewski, Redwood City, CA (US); James Weaver, Morgan Hill, CA (US); George John D'Ambrosio, Chicago, IL (US); Manish Patel, Scotts Valley, CA (US); Kim Hixson, San Carlos, CA (US)

(73) Assignee: Omnicell, Inc., Mountain View, CA (US)

( * ) Notice: Subject to any disclaimer, the term of this patent is extended or adjusted under 35 U.S.C. 154(b) by 1528 days.

(21) Appl. No.: 14/084,967

(22) Filed: Nov. 20, 2013

(65) Prior Publication Data

US 2014/0074284 A1 Mar. 13, 2014

Related U.S. Application Data

(63) Continuation of application No. 13/705,964, filed on Dec. 5, 2012.

(Continued)

(51) Int. Cl.
*G06F 19/00* (2018.01)
*G06Q 10/08* (2012.01)
(Continued)

(52) U.S. Cl.
CPC .......... *G06F 19/3462* (2013.01); *G06F 19/00* (2013.01); *G06Q 10/087* (2013.01); *G07F 17/0092* (2013.01); *G16H 40/20* (2018.01)

(58) Field of Classification Search
CPC .. G06F 19/3462; G06F 19/00; G07F 17/0092; G06Q 10/087; G16H 40/20
(Continued)

(56) References Cited

U.S. PATENT DOCUMENTS 5,701,252 A * 12/1997 Facchin .................... G07F 9/02
235/375
5,842,976 A * 12/1998 Williamson ........ G06F 19/3418
600/300

(Continued)

FOREIGN PATENT DOCUMENTS

CN 1541898 A 11/2004
CN 101010115 A 8/2007
(Continued)

OTHER PUBLICATIONS

NIST/SEMATECH e-Handbook of Statistical Methods, http://www.itl.nist.gov/div898/handbook/ Jan. 23, 2011.*
(Continued)

*Primary Examiner* — Ashford S Hayles
(74) *Attorney, Agent, or Firm* — Kilpatrick Townsend & Stockton LLP

(57) ABSTRACT

Dispensing units or stations for dispensing items, such as in a healthcare facility, are linked in a network. The dispensing stations are arranged in groups. Inventory data for all the stations in a group is combined together, and displayed at a graphical view or widget. Multiple widgets may be displayed on a dashboard screen of a user system, for use in managing inventory.

25 Claims, 16 Drawing Sheets

Related U.S. Application Data

(60) Provisional application No. 61/566,957, filed on Dec. 5, 2011.

(51) Int. Cl.
*G07F 17/00* (2006.01)
*G16H 40/20* (2018.01)

(58) Field of Classification Search
USPC ............................................... 705/28
See application file for complete search history.

(56) References Cited

U.S. PATENT DOCUMENTS

| | | | | |
|---|---|---|---|---|
| 5,970,471 | A * | 10/1999 | Hill | G06Q 30/02 705/26.8 |
| 6,339,732 | B1 * | 1/2002 | Phoon | A61J 7/0084 700/237 |
| 6,580,968 | B1 * | 6/2003 | Yuyama | G07F 5/18 700/241 |
| 6,842,736 | B1 * | 1/2005 | Brzozowski | G06Q 10/10 705/1.1 |
| 7,499,769 | B2 | 3/2009 | Walker et al. | |
| 7,685,026 | B1 * | 3/2010 | McGrady | G06Q 10/08 705/28 |
| 7,826,923 | B2 | 11/2010 | Walker et al. | |
| 8,069,239 | B2 * | 11/2011 | Trochman | G08C 19/00 348/135 |
| 8,249,956 | B1 * | 8/2012 | Barua | G06Q 10/08 705/22 |
| 8,606,596 | B1 * | 12/2013 | Bochenko | G06Q 10/00 705/2 |
| 8,738,177 | B2 | 5/2014 | van Ooyen et al. | |
| 8,806,225 | B2 * | 8/2014 | Park | G06F 21/74 713/193 |
| 2002/0032582 | A1 * | 3/2002 | Feeney, Jr. | G06F 19/3462 705/2 |
| 2002/0065724 | A1 * | 5/2002 | Tsuruda | G06Q 10/087 705/16 |
| 2002/0128932 | A1 * | 9/2002 | Yung | G06Q 10/087 705/26.1 |
| 2003/0050731 | A1 * | 3/2003 | Rosenblum | G06F 19/3462 700/232 |
| 2003/0220713 | A1 * | 11/2003 | Owens | G07F 9/02 700/236 |
| 2004/0093340 | A1 * | 5/2004 | Edmondson | G06Q 10/10 |
| 2005/0261940 | A1 * | 11/2005 | Gay | G06Q 50/24 705/3 |
| 2006/0219517 | A1 * | 10/2006 | Cheng | G07F 9/026 194/217 |
| 2006/0247823 | A1 * | 11/2006 | Boucher | G07F 5/18 700/241 |
| 2007/0208598 | A1 * | 9/2007 | McGrady | G06F 19/3462 705/3 |
| 2008/0316045 | A1 * | 12/2008 | Sriharto | G06Q 50/22 340/10.1 |
| 2008/0319579 | A1 | 12/2008 | Vahlberg et al. | |
| 2009/0013028 | A1 * | 1/2009 | Canter | H04L 67/02 709/203 |
| 2009/0048712 | A1 | 2/2009 | Rosenblum | |
| 2009/0089187 | A1 * | 4/2009 | Hoersten | G06Q 10/087 705/28 |
| 2010/0145506 | A1 | 6/2010 | Waugh et al. | |
| 2010/0198401 | A1 | 8/2010 | Waugh et al. | |
| 2011/0054935 | A1 | 3/2011 | Hardaway | |
| 2011/0161108 | A1 * | 6/2011 | Miller | G06Q 10/10 705/3 |
| 2011/0251850 | A1 | 10/2011 | Stephens | |
| 2011/0288886 | A1 * | 11/2011 | Whiddon | G06F 19/328 705/3 |
| 2012/0004770 | A1 * | 1/2012 | Ooyen | G07F 11/58 700/235 |
| 2013/0070090 | A1 * | 3/2013 | Bufalini | G16H 20/13 348/143 |
| 2013/0124227 | A1 * | 5/2013 | Ellis | G06Q 50/22 705/3 |
| 2013/0139234 | A1 * | 5/2013 | Inbaraj | G06F 21/305 726/7 |
| 2013/0346261 | A1 * | 12/2013 | Phillips | G06K 9/00771 705/28 |

FOREIGN PATENT DOCUMENTS

| | | | | |
|---|---|---|---|---|
| CN | 101488253 A | 7/2009 | | |
| JP | 2005-038256 A | 2/2005 | | |
| JP | 2010-530781 A | 9/2010 | | |
| WO | WO 2011130177 A1 * | 10/2011 | | G07F 9/026 |
| WO | WO-2011130177 A1 * | 10/2011 | | G07F 9/026 |

OTHER PUBLICATIONS

Author Unknown, "Ask Dr. Math: Questions & Answers from our Archives," The Math Forum, Feb. 14, 2000, 4 pages. Retrieved on Nov. 19, 2012 from: http://mathforum.org/library/drmath/view/52188.html.

Author Unknown, "How to Interpret a Box Plot in Terms of a Normal Distribution," Department of Mathematics & Statistics, McMaster University, Sep. 21, 1999, 2 pages. Retrieved on Nov. 20, 2012 from: http://www.math.mcmaster.ca/peter/s2ma3/s2ma3_9798/boxplots.html.

Extended European Search Report for European Patent Application No. 12779388.3 dated Oct. 27, 2015, all pages.

Office Action for Chinese Patent Application No. 201280033147.X dated Dec. 11, 2015, all pages.

Non-Final office action for U.S. Appl. No. 13/705,964, dated Nov. 20, 2015, all pages.

Office Action dated Jan. 19, 2016 for Japanese Patent Application No. 2014-509387, all pages.

\* cited by examiner

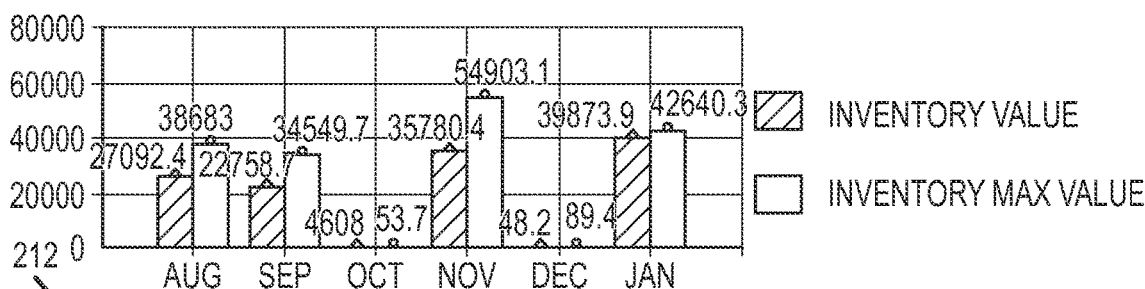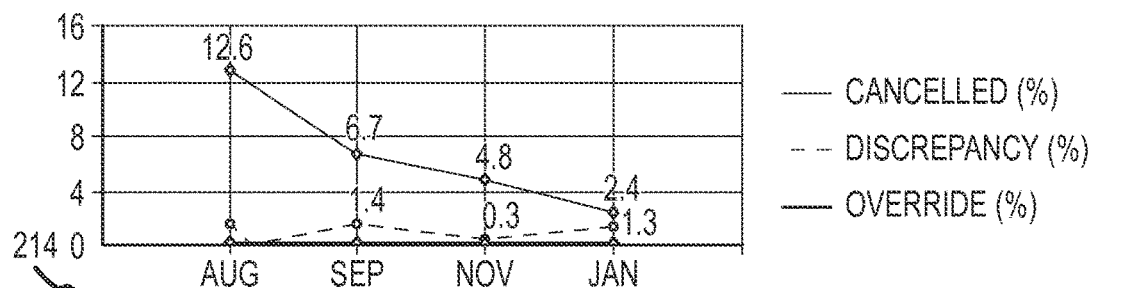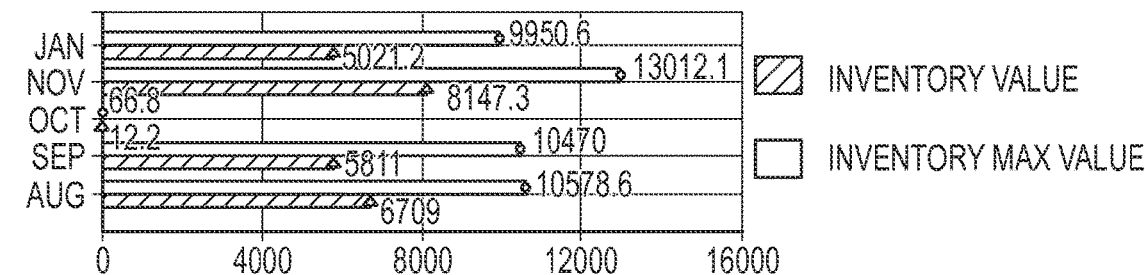
FIG.2a

520

CONTINUED FROM FIG.5A

CABINET WATCH LIST

SELECTED CRITERIA:
DATE PERIOD BETWEEN 8/1/2010 AND 8/31/2010
NURSING UNITS IN (95MS; 75MS; 64MS; 65MS; 55MS; 54MS; 11MS)

| STATION | % ACTIVE ITEMS | % IDLE ITEMS | VALUE ON HAND | VALUE AT MAX | VALUE ABOVE MAX |
|---|---|---|---|---|---|
| UF54A | 100 | 0 | $4,684 | $7,601 | ($2,916) |
| UF74ADA | 100 | 0 | $2,991 | $4,482 | ($1,491) |
| UF64CATHY | 100 | 0 | $2,762 | $3,715 | ($953) |
| UF75A | 100 | 0 | $2,639 | $3,833 | ($1,194) |
| UF54C | 100 | 0 | $2,625 | $3,756 | ($1,132) |
| UF74BETSY | 100 | 0 | $2,591 | $3,475 | ($884) |
| UF115B | 100 | 0 | $2,462 | $4,026 | ($1,563) |
| UF65B | 100 | 0 | $2,367 | $3,548 | ($1,182) |
| UF95D | 100 | 0 | $2,365 | $3,048 | ($683) |
| UF64AUDREY | 100 | 0 | $2,307 | $3,259 | ($952) |
| UF115A | 100 | 0 | $2,180 | $3,019 | ($838) |
| UF75B | 100 | 0 | $2,095 | $2,771 | ($676) |
| UF55A | 100 | 0 | $1,959 | $2,855 | ($896) |
| UF74CARLY | 100 | 0 | $1,937 | $2,632 | ($695) |
| UF65A | 100 | 0 | $1,907 | $3,072 | ($1,165) |
| UF75C | 100 | 0 | $1,885 | $2,687 | ($802) |
| UF95B | 100 | 0 | $1,843 | $3,008 | ($1,165) |
| UF95C | 100 | 0 | $1,779 | $2,634 | ($855) |
| UF95A | 100 | 0 | $1,660 | $2,084 | ($424) |
| UF55B | 100 | 0 | $1,398 | $1,878 | ($480) |
| UF54B | 100 | 0 | $1,382 | $1,784 | ($402) |
| UF64BERTHA | 100 | 0 | $1,324 | $2,048 | ($724) |
| UF55C | 100 | 0 | $1,311 | $2,046 | ($735) |

FIG.5B

WHISPERING SPRINGS HOSPITAL

ISSUE COMPLIANCE

SELECTED CRITERIA:
DATE PERIOD BETWEEN 8/1/2010 AND 8/31/2010
TRANSACTION TYPES IN (SUPPLEMENTAL RESTOCK; RETURN; ISSUE)

720

| STATION | COST STATION | ISSUE COMPLIANCE (%) | ISSUE COMPLIANCE BILLABLE (%) | ISSUE COMPLIANCE NON-BILLABLE (%) |
|---|---|---|---|---|
| OCBLUE1 | 1 | 18.33 | 18.33 | 0.00 |
| OCCTSURE1 | 1 | 36.00 | 36.00 | 0.00 |

FIG.7a

| USER WATCH LIST - AnomalousUsage | | |
|---|---|---|
| SELECTED CRITERIA: DATE PERIOD BETWEEN 11/1/2010 AND 11/30/2010 NURSING UNITS IN (6S-6; 11MS) | | |
| USER NAME | AU EXTREME OUTLIERS FROM WITHDRAWN FOR NARCOTICS | AU MILD OUTLIERS FROM WITHDRAWN FOR NARCOTICS |
| McRAE, EVANDER J. | 2 | 3 |
| PARSON, DREXEL K. | 1 | 1 |
| OGLE, TAREKE F. | 1 | 1 |
| DAYANIN, CLARISSA W. | 1 | 0 |
| RIVERO, TIKVA T. | 1 | 1 |
| BASKERVILLE, SHANTRESE V. | 1 | 2 |
| BUCKLEY, SCHWANA B. | 1 | 2 |
| NICKEL, SHAJUAN C. | 1 | 2 |
| KILMANN, SHERELLE E. | 1 | 1 |

FIG. 11

SYSTEM AND METHOD FOR MANAGING INVENTORY AT DISPENSING UNITS

CROSS REFERENCES TO RELATED APPLICATIONS

This application is a continuation of U.S. application Ser. No. 13/705,964 filed on Dec. 5, 2012, which claims the benefit of and is a non-provisional of U.S. Provisional Application Ser. No. 61/566,957 filed on Dec. 5, 2011, both of which are hereby expressly incorporated by reference in their entirety for all purposes as if fully set forth herein.

BACKGROUND OF THE INVENTION

The present invention relates generally to item dispensing, and in particular to systems and methods for managing inventory at dispensing units, such as a dispensing units in a medical or other healthcare facility.

Medical facilities, such as hospitals, use dispensing stations or units to facilitate the delivery of medicines, supplies and other items. Such dispensing units may be placed near patients and are designed to hold various supplies and pharmaceuticals needed by those patients. The dispensing units have the ability to control access and maintain records on the number and types of items that are dispensed, using a data input and processing system built into the unit. For example, a dispensing unit may include a cabinet with a plurality of retractable drawers. Each drawer can be divided into bins, so that more than one type of item may be held within each drawer in order to facilitate the delivery of one or different items to a single patient or to a group of patients in nearby locations. Security may be provided by providing locks on the drawers to allow access to certain individuals, such a nurses, or allow access to only certain items, or allow access only at certain times of the day, all under the control of the system at the station.

In order to access items in a dispensing unit, an authorized individual may be required to enter various information, such as authenticating information (e.g., a user ID/password of the authorized individual), information concerning the patient (e.g., patient name or ID), and information concerning the item being dispensed (name or identifier of item). Data can be scanned (e.g. from a bar code) or entered at a keyboard. Other information is collected by the system at the dispensing unit, such as the time that each item is dispensed.

Thus, large amounts of information are gathered as items are dispensed, such as quantity and types of items dispensed, for whom dispensed, when dispensed, when replenished, and so forth. However, that information is often difficult to analyze for purposes of inventory management and analysis, other than through complex spreadsheets and other reports that may not be easily used by supply technicians (people replenishing cabinets) and others involved in managing inventory.

In addition, conventional inventory reporting systems are often not suitable for tracking pharmaceuticals and other supplies in a medical facility, such as a hospital, where there can be significant differences in the level of care provided where dispensing stations are located. Some locations may have predictable and routine uses of supplies (making inventory management somewhat straight forward), but other locations (such as at emergency and critical care units) may be difficult to manage. For example, nurses in emergency and critical care locations might need supplies quickly and have little time to enter data for items being dispensed. It can also be difficult at those locations to predict, at any point in time, the type and quantity of items that may be needed. Thus, unlike routine medical care locations, supplies for higher levels of care may need to be monitored frequently and always fully stocked to assure immediate availability when needed. At the same time, inventory managers need to monitor dispensing stations at all levels of care to avoid mismanagement of supplies by users and, especially, improper diversion of addictive items, such as narcotics, that may be stocked at the dispensing stations.

BRIEF SUMMARY OF THE INVENTION

There is provided, in accordance with embodiments of the present invention, a network/system and method for displaying, in the form of graphical views or widgets, inventory data for dispensing stations arranged in groups. The inventory data for all the dispensing stations in one group are combined and displayed together in one graphical view.

In one embodiment, a dispensing system comprises a plurality of dispensing stations, each station having a plurality of storage locations for storing items. The stations are arranged in a plurality of station groups, with each station group including one or more of the stations. A database stores inventory data relating to the items stored at the stations. A processor is programmed to display at a display device a graphic view of inventory data for all stations in one station group.

A more complete understanding of the present invention may be derived by referring to the detailed description of the invention and to the claims, when considered in connection with the Figures.

BRIEF DESCRIPTION OF THE DRAWINGS

FIGS. 2a and 2b are enlarged views of graphical views or widgets seen in the dashboard screen of FIG. 2.

FIGS. 5a and 5b illustrate two widgets and a cabinet watch list containing detailed information relating to data displayed in the two widgets.

FIG. 7a illustrates a compliance list for individual dispensing stations, showing compliance data relating to a widget such as the widget illustrated in FIG. 7.

FIG. 11 illustrates a user watch list displayed in response to selection of a month of data in the graphical view of FIG. 9.

DETAILED DESCRIPTION OF THE INVENTION

Figure 1:
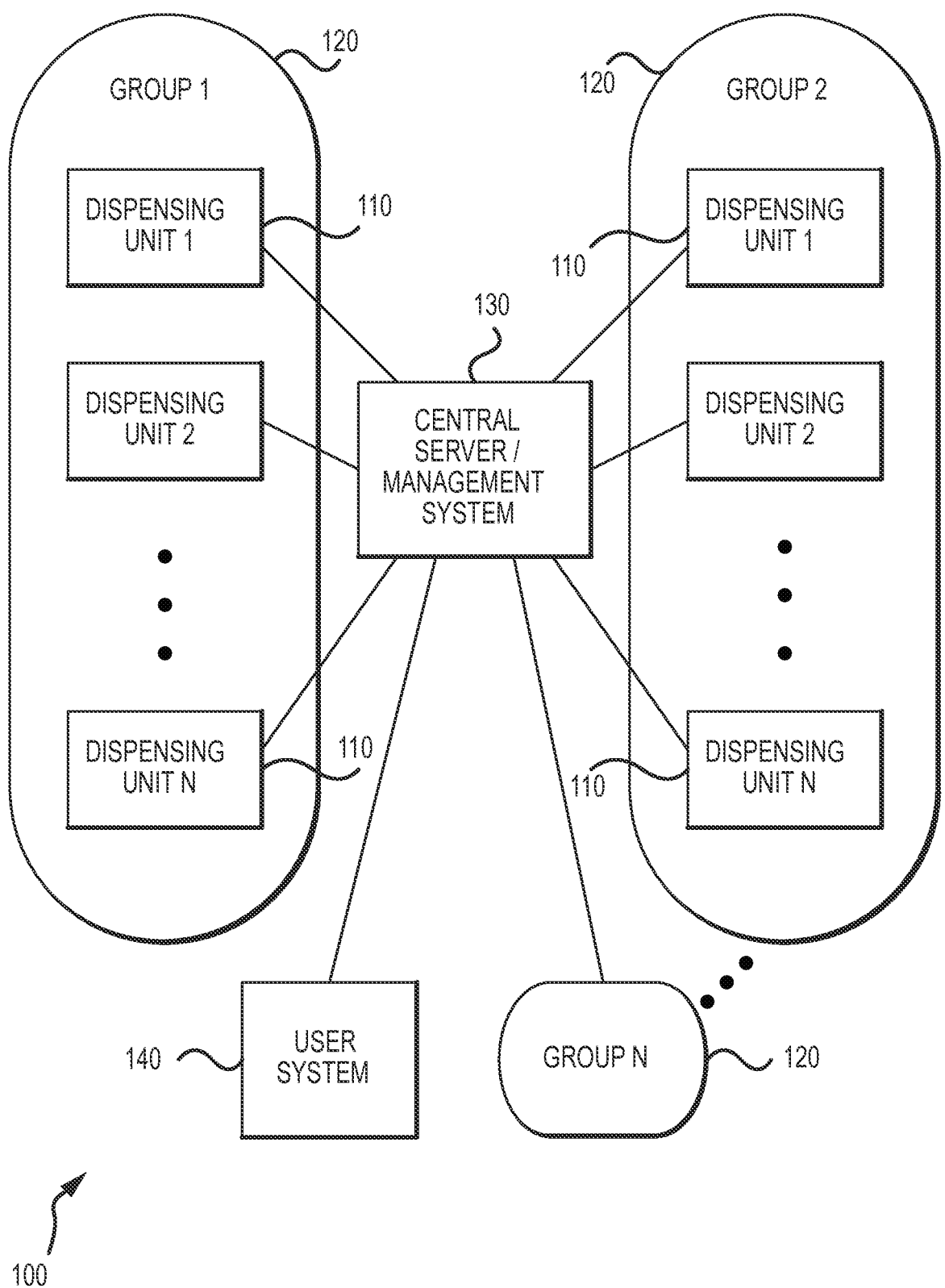
FIG. 1 illustrates a network of dispensing units, a central server system, and a user system, in accordance with an embodiment the present invention.

Generally speaking, embodiments of the present invention provide methods and systems for managing inventory relating to units or stations that dispense items, such as medical supplies and pharmaceuticals dispensed to a nurse or other provider within a medical or other healthcare facility. The system may be implemented as a network with a plurality of linked dispensing stations or units.

In some embodiments, the dispensing stations in the network are arranged or grouped within a medical facility. As an example, stations within one general location (floor, wing, etc.) may be grouped together in one station group. As another example, stations located within certain departments or organizations at the facility may be grouped together (critical care, medical surgery, emergency room, operating room, outpatient clinic, and so forth). A user managing inventory may want to view inventory data for all stations within a station group, and in some instances, within multiple station groups.

In one embodiment a user may view, at a display device, inventory data in the form of a "widget" or graphical view, in order to manage inventory stored at dispensing stations in one group. As an example, a widget may represent inventory data pertaining to how often requested items are out of stock ("stock outs") in a selected group of stations (e.g., stations for which the user has responsibility). The user may also view, perhaps simultaneously, a widget representing data pertaining to how often items are dispensed or withdrawn from the stations in relation to how often those items are replenished (referred to as a "withdrawn-refilled ratio"). A withdrawn-refilled ratio preferably reflects items being much more frequently withdrawn than replenished, since items should be replenished in sufficient quantities between re-stocking visits.

The data is displayed in the form of visual graphics or "widgets," so they can be conveniently appreciated and analyzed by the user. However, the user may have responsibility for more than one group of stations. In this embodiment, a selection menu is provided to give the user the opportunity change the widget or graphical view in order to see, for example, the same type of data (and same graphical views) for a different group of stations. By selecting a different group to be viewed, the same type of data (for the next group) is displayed in the same way, again providing a way to conveniently see and analyze the data in graphical form (and compare it to other station groups). Thus, in a broad sense, this embodiment provides inventory data to be shown as a graphical view for any station group and, through the use of a selection menu, provide a means to change the station group to easily and conveniently view the same type of data (and graphical view), but for a different station group, and provide a quick visual comparison of historical trends.

The grouping of dispensing stations can be useful in the management of inventory. In one embodiment, dispensing stations located where emergency or acute care is provided are grouped separately from other dispensing stations in the facility (e.g., those located where general or less intensive care is provided). Dispensing stations involving emergency or acute care typically have inventory levels that are more difficult to predict (sometimes requiring higher levels of stock to avoid depletion during emergencies). Workflow compliance, such as requiring nurses to enter data (scanning bar codes and the like), can be more difficult at such stations because of the circumstances surrounding the level of care provided, particularly the urgent need for items during that care. By grouping stations according to the level of care (e.g., stations at locations requiring a higher level of care are grouped together), inventory can be more effectively managed using the techniques described herein.

In another embodiment, inventory data (such as cost data) for a group of stations may also be displayed as a graphical view at a display device, but with cost of inventory considered in a number of different ways. For example, the total cost of items can be calculated in different ways using different cost bases or cost definitions, to give different perspectives on how the cost of inventory is being managed. In this embodiment, for example, total cost can be calculated using a "first cost" for each item (based on the earliest date during a specified period of time that an item was placed in the station group), a "last cost" for each item (based on the most recent date during a specified period of time that an item was placed in the station group), an average cost for each item over a specified period of time, a max cost for each item (based on the highest cost of an item during a specified period of time that the item was placed in the station group), or a minimum cost for each item (based on the lowest cost for an item placed in the station group). In this embodiment, a user may display the total cost of inventory within a station or a group of stations based on any one of the cost definitions, as applied to all items (in some embodiments the cost definitions may be applied to a subset of items/stations or groups). Using these different cost calculations provides a user with a perspective on how costs may impact inventory management and decisions relating to inventory. For example, if looked at in the context of "first cost," the user can see how much inventory is being maintained based on initial costs during a specified period of time. If then looked at in the context of "last cost," the user may see how much inventory is being maintained based on the final cost of each item placed in the station. As should be apparent, if the cost of the particular item is increasing, the user will be able to appreciate, from comparing "first cost" and "last cost" views, that the total cost of maintaining the inventory is significantly increasing and that inventories maintained at dispensing station should perhaps be reduced (particularly if there have not been significant "stock outs"). In some embodiments, a user may understand price increases well enough to choose one of the cost definitions for most or all displays of inventory data, where that particular definition best represents the value of the inventory being managed.

In another embodiment, a user at a display device may view data (in the form or a widget or graphical view) for both (1) a total cost of all items stored at a selected station group (or individual station) over a specified period of time, and (2) a PAR value of all items stored at the selected station group (or station). The PAR value (sometime referred to as "max value") represents a desired cost, as established by the user, of all items stored at the selected station group. When a dispensing unit is replenished, the supply technician or other person involved in replenishment will typically replenish the cabinet to the "PAR" value. By displaying both actual inventory value data and PAR value data, a user may be able to conveniently manage and reduce the cost of inventory. For example, if the actual total cost is consistently below the PAR value, the user may determine that the PAR value can be reduced (thus reducing the number and cost of items required during restocking or replenishment) in order to reduce the costs associated with maintaining inventory at that dispensing station or group of stations (especially if there have not been a significant number of "stock outs" associated with the dispensing station).

In yet another embodiment, a user at a display device may view inventory data (in the form of a widget or graphical view), while at the same time viewing or having access to compliance data that has a bearing on the accuracy of the inventory data in question. As an example, audits are periodically conducted at dispensing stations within a medical facility to determine if the inventory actually present at the station is consistent with the inventory that should be present according to reported data from the station (e.g., data based on reported withdrawals and restocking of items). If there are inconsistencies, the discrepancy for the station is noted (and stored as data at central server 130). Thus, a user viewing a widget, say, representing inventory costs or amounts over a specified period of time for a given station group (or a given individual station), and desiring to make inventory adjustments to improve efficiency of inventory costs (e.g., reducing the PAR value) at that group of stations, might look at the compliance data for that group prior to making a decision. This is facilitated by the user viewing both the inventory data in question for a given dispensing station group and the compliance data for that same group (both displayed as widgets or graphical views) for a given period of time, and if there are significant compliance issues observed (e.g., high discrepancies) in connection with the given station group for the same period of time, the user will know that the underlying inventory data may not be reliable or accurate (and perhaps decisions should not be made based on the displayed inventory data, at least not without further investigation).

In one embodiment, discrepancy data could be used to reduce costs associated with consigned supplies (items, often very costly, that are provided by a supplier for the dispensing stations, but not charged for until the supply is used (dispensed or found during audit to no longer be at the dispensing station). As should be apparent, if such items are removed without pertinent data being entered (e.g., identifying the patient for whom it is being dispensed), the medical facility must pay for the supply but has no mechanism for recovering the cost. Using compliance data, the inventory manger can identify the discrepancy and take appropriate action (e.g., training nurses using that dispensing station to enter data for those items at the time of dispensing).

In another embodiment, a statistical analysis method using a box plot (also known as a "box and whiskers plot") can be applied to easily identify significant discrepancies and non-compliance. Such issues can be particularly significant when they arise in connection with certain types of supplies (e.g., substances than can be addictive), because significant departures from normal data may be the first indicator of improper diversion of supplies by a person having access to a dispensing station. The box plot technique greatly facilitates the identification of "outliers" in analyzing data, particularly over more traditional techniques involving use of standard deviations (e.g., how many standard deviations a given data value may be above or below an average value).

Referring now to FIG. 1, there is illustrated a dispensing network 100 that includes a plurality of dispensing stations or units 110, such as may be located within a medical facility. While not illustrated, the dispensing units may each include a cabinet having a plurality of retractable drawers secured by locks and that can be opened only when an authorized user is granted access using a data entry and processing system at the dispensing unit. One exemplary type of drawer system in a dispensing unit is described in commonly owned U.S. Pat. No. 6,039,467, issued on Mar. 21, 2000 to Holmes. Alternative types of dispensing units/cabinets are described in commonly owned U.S. Pat. No. 6,272,394, issued on Aug. 7, 2001 to Lipps, U.S. Pat. No. 5,805,456, issued on Sep. 8, 1998 to Higham et al, U.S. Pat. No. 5,745,366, issued on Apr. 28, 1998 to Higham et al., and U.S. Pat. No. 5,905,653, issued on May 18, 1999 to Higham et al. All of the forgoing commonly owned patents are hereby incorporated by reference.

Also seen in FIG. 1 is a central server/management system 130 to which each of the dispensing units is linked, such as by wireless communications. As will be more fully described later, the central server 130 manages the overall operation of the network 100, including receiving data from the dispensing units 110 as stored items are withdrawn or removed, and then subsequently replenished. Such data is stored in a database (not illustrated) associated with the central server 130.

As illustrated in FIG. 1, the dispensing units 110 are organized in groups 120 (Group 1 through Group N), with each dispensing unit assigned to one of the groups 120 in the illustrated embodiment. As mentioned earlier, the groups could be established for different locations or departments within a medical facility.

As also mentioned earlier, the grouping of units 110 permits a person responsible for inventory to view and manage inventory data all those units within his or her area of responsibility. Further, the responsibility may include different levels of responsibility. For example, there may be several individuals (e.g., inventory supply technicians) that are each responsible for inventory for one (or a few) groups 120, and a supervisor that has more general responsibility for inventory for a larger number of groups 120. In setting up viewing rights, each user may establish viewing rights (for inventory data) for only those groups 120 for which he or she has responsibility, with a supervisor having viewing rights for a much larger number of groups 120.

Also seen in FIG. 1 is a user system 140, at which users (e.g., individual supply technicians, supervisors, or other personnel involved in inventory management) may access inventory data stored at the central server 130. As should be appreciated, there may be a number of user systems 140 within network 100, depending on the number of users needing to view data.

As mentioned earlier, in one embodiment the dispensing units may be organized and grouped according to the level of medical care provided in the areas where the stations or units 110 are located. For example, Group 1 may represent units located at areas where acute care required, such as care resulting from more sudden or severe health conditions. Such care could be required in an intensive care department or an emergency room department within a hospital. Thus, these dispensing units may involve items that might be needed very quickly, or that have patterns of use that make difficult a prediction of how often or how frequently items may be needed (i.e., the predictability of inventory is lower). Accordingly, in accordance with such embodiment, there may be needed a higher supply level of various items to prevent stock outs (not having available an urgently needed item could have serious consequences). In addition, in departments having a higher level of care, a nurse or other person urgently needing an item from a dispensing unit may have little time to enter data normally required for dispensing the item (the nurse may override the system in order to quickly dispense an item). As a result, when reviewing inventory data at such a station group, higher levels of cost involved in stocking some or all of the items stored may need to be tolerated, and discrepancies (as reflected in reported compliance data—to be described later) may be higher without causing inventory management concerns. Also, when comparing data at user system 140, comparing stations and station groups having similar levels of care is often more useful than stations or station groups having different levels of care.

In the described embodiment, in Group 2 may represent units located in areas where less acute care (a lower level of care) is needed. Such areas having a lower level of care might be departments providing routine or minor surgeries or providing general patient care.

Of course, it should be appreciated that in a typical large hospital, there might be hundreds of dispensing stations, arranged in many different groups. The groups could be organized by location, level of care and other categories that would provide the most useful data for comparison to personnel responsible for inventory management.

One advantage of grouping dispensing units by level of care is that it permits more accurate assessment of inventory conditions. Dispensing units having similar types of dispensing activity (located in areas having similar levels of care) can be compared. For example, unusually high numbers of withdrawals from high care dispensing units having normally higher levels of non-compliance are (when grouped together) less likely to be obscured by other dispensing units at locations having lower levels of care. Further, suspicious withdrawals at a given dispensing unit are much more likely to be identified as suspicious when compared to other dispensing units located in areas where similar levels of care are being provided. In addition, "outliers" (suspicious activity far outside the norm) can be more readily identified and analyzed using, for example, a box plot analysis that will be described later, when stations involving similar levels of care are grouped together.

Figure 2:
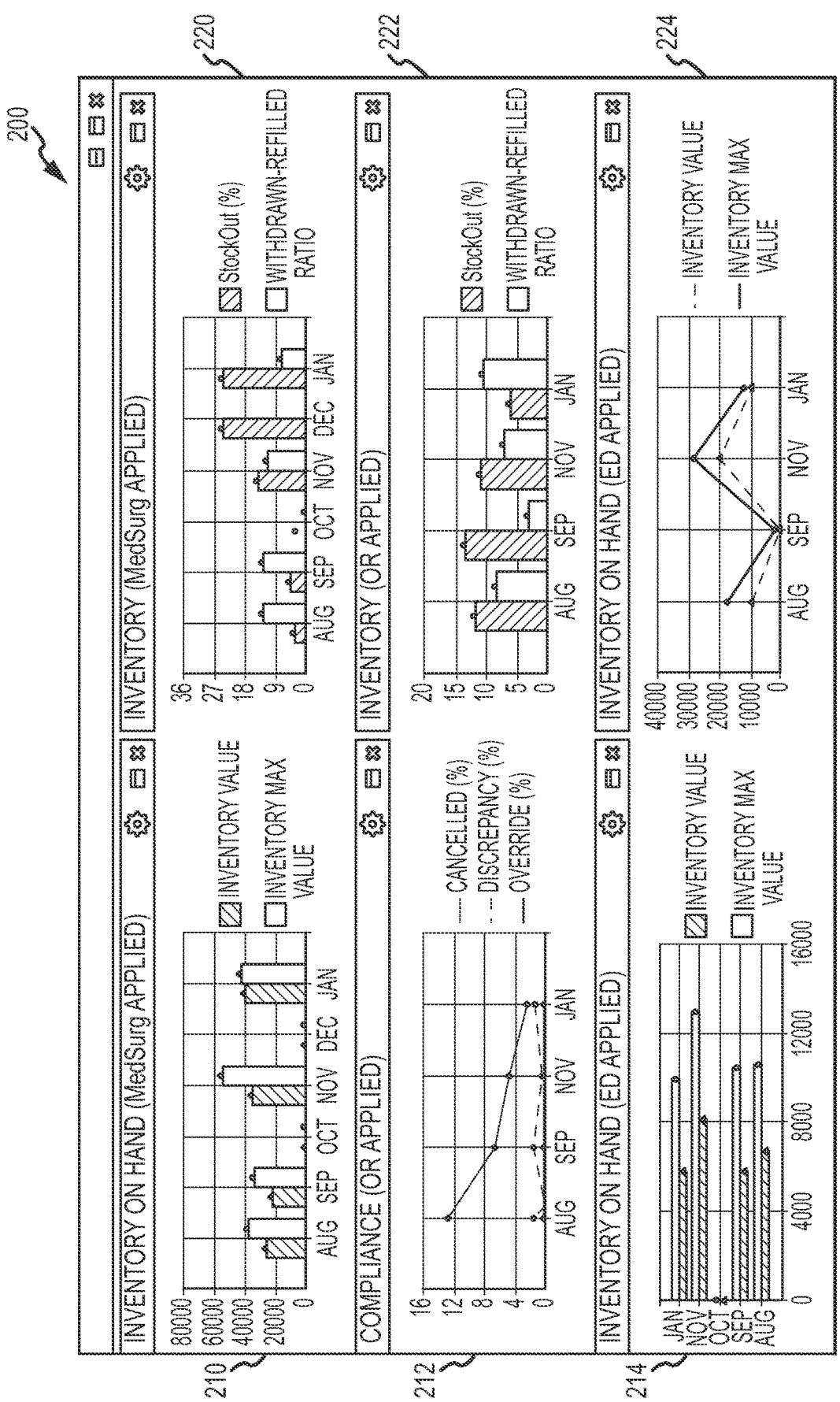
FIG. 2 is a dashboard screen seen on a display device of the user system in the network of FIG. 1.

FIG. 2 illustrates a "dashboard" display or screen 200, such would be seen by a user at the user system 140. As illustrated, the dashboard 200 includes six widgets 210, 212, 214, 220, 222, and 224. In general, a widget is a graphical view, typically framed in a box or similar geometrical shape that appears on a screen. In the network 100, it is implemented by software applications running on the user system 140, using data (and in some instances, software code) supplied by central server 130. In described embodiments, the inventory data collected by the central server 130 is processed and arranged to be presented to the user as a widget on the display of the user system 140. As should be appreciated as this description progresses, the presentation of data in the form of a widget or graphical view is much easier for a user to quickly understand and apply, in order to manage inventory (and make decision regarding inventory) at the dispensing units 110. Also, widgets (or views) may have "click and drag" features to permit the widgets to be re-arranged on a screen (e.g., for related widgets to be more easily compared to each other by the user), and have associated software features that permit a user to easily access and view underlying and more detailed data associated with the widget, such as by clicking on bars, graphs or lines within the widget.

The widgets 210, 212 and 214 are shown enlarged in FIG. 2a. Widget 210 displays vertical bars ("Inventory Value" and "Inventory Max Value") representing inventory value on hand (monthly average) and PAR value for dispensing units at a group identified as "MedSurg Applied" for the months of August through January.

Widget 212 displays line graphs representing compliance data for the same months for a group identified as "OR Applied." The use of compliance data will be described later in conjunction with FIG. 7. Briefly, the compliance data in FIG. 2 is shown in three forms: Cancelled (%), Discrepancy (%) and Override (%). Cancelled indicates the percentage of visits to a dispensing unit where the cabinet was opened by a nurse, but then the withdrawal was cancelled (indicating the nurse did not remove an item). Discrepancy indicates the percentage of time that an audit reveals a discrepancy between the number of items reported as removed when the cabinet is accessed, but in a subsequent manual audit (e.g., during a replenishment visit), the number of items in the cabinet does not agree with the reported withdrawals (and replenishments). Override indicates that a nurse accessed a unit 110 but there was no order for the item removed (received by the unit 110 or the central server 130 in advance of the withdrawal). Typically this condition may legitimately arise in medical emergencies (e.g., emergency room or operating room) when there is no time to place an order, but in some instances it may represent suspicious removal of items (Note in FIG. 2a that the override percentage values are all close to zero and are thus obscured by the horizontal axis). All three of these data categories (Cancelled, Discrepancy and Override) will impact the accuracy of inventory data (i.e., inventory data displayed may need to be considered unreliable if the compliance data indicates low reliability). The three compliance data categories are displayed separately in widget 212. However, in some embodiments different forms of compliance data could be combined (as a composite value) into a single line, bar or other representation of data.

Widget 214 displays horizontal bars ("Inventory Value" and "Inventory Max Value") representing inventory on hand for items at a group identified as "ED Applied" for the months of August through January.

Figure 2B:
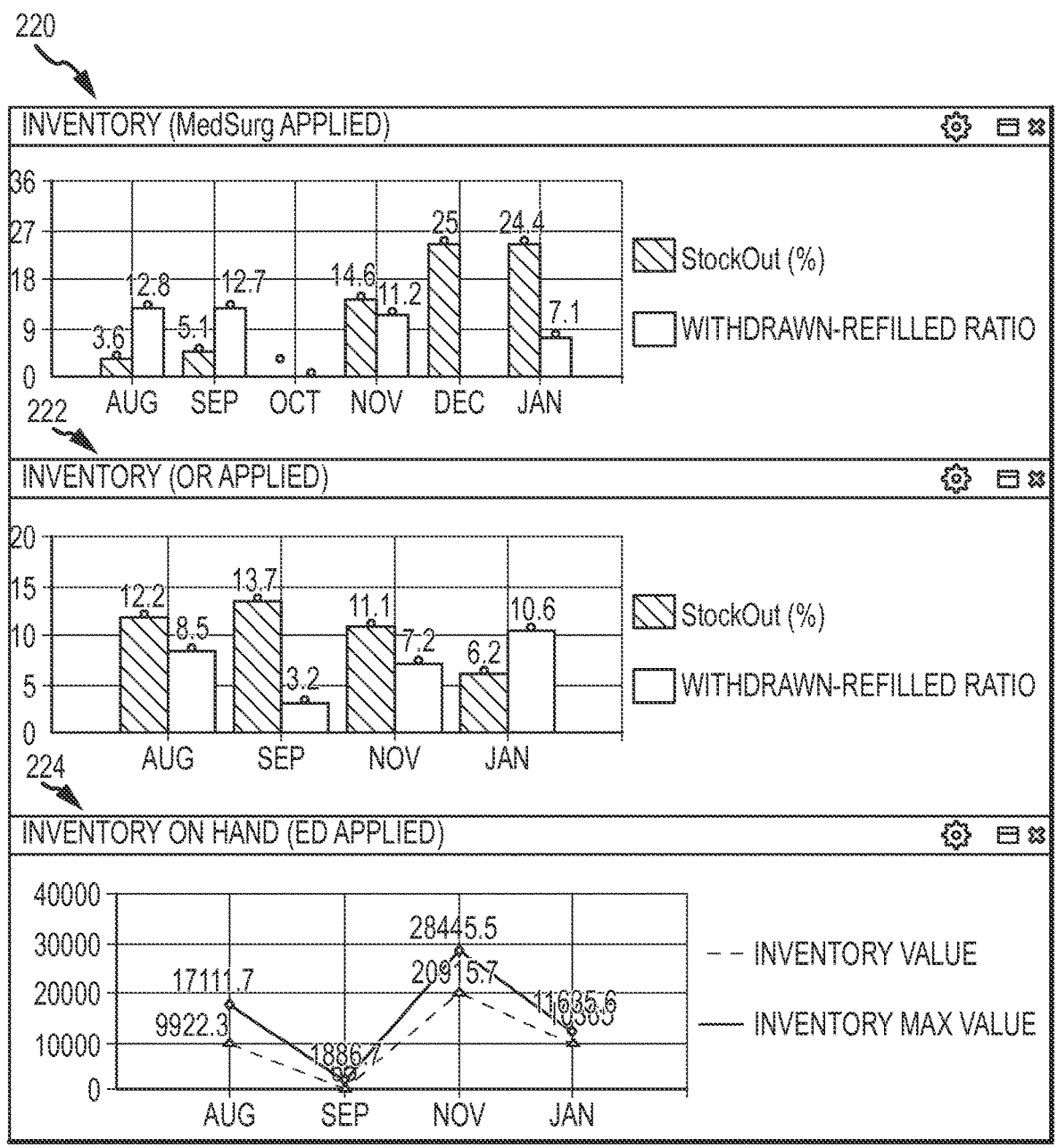

The widgets 220, 222 and 224 are shown enlarged in FIG. 2b. Widget 220 displays vertical bars ("Stock Out (%)" and "Withdrawn-Refilled Ratio") for inventory at a group identified as "MedSurg Applied" for the months of August through January. Widget 222 displays vertical bars ("Stock Out (%)" and "Withdrawn-Refilled Ratio") for inventory at a group identified as "OR Applied" for the months of August through January. Widget 224 displays line graphs ("Inventory Value" and "Inventory Max Value") representing inventory on hand for items at a group identified as "OR Applied" for the months of August through January.

As should be appreciated, a user seeing dashboard display 200 would have established viewing rights for inventory data for several groups of dispensing units (MedSurg Applied, OR Applied, and ED Applied).

Figure 3:
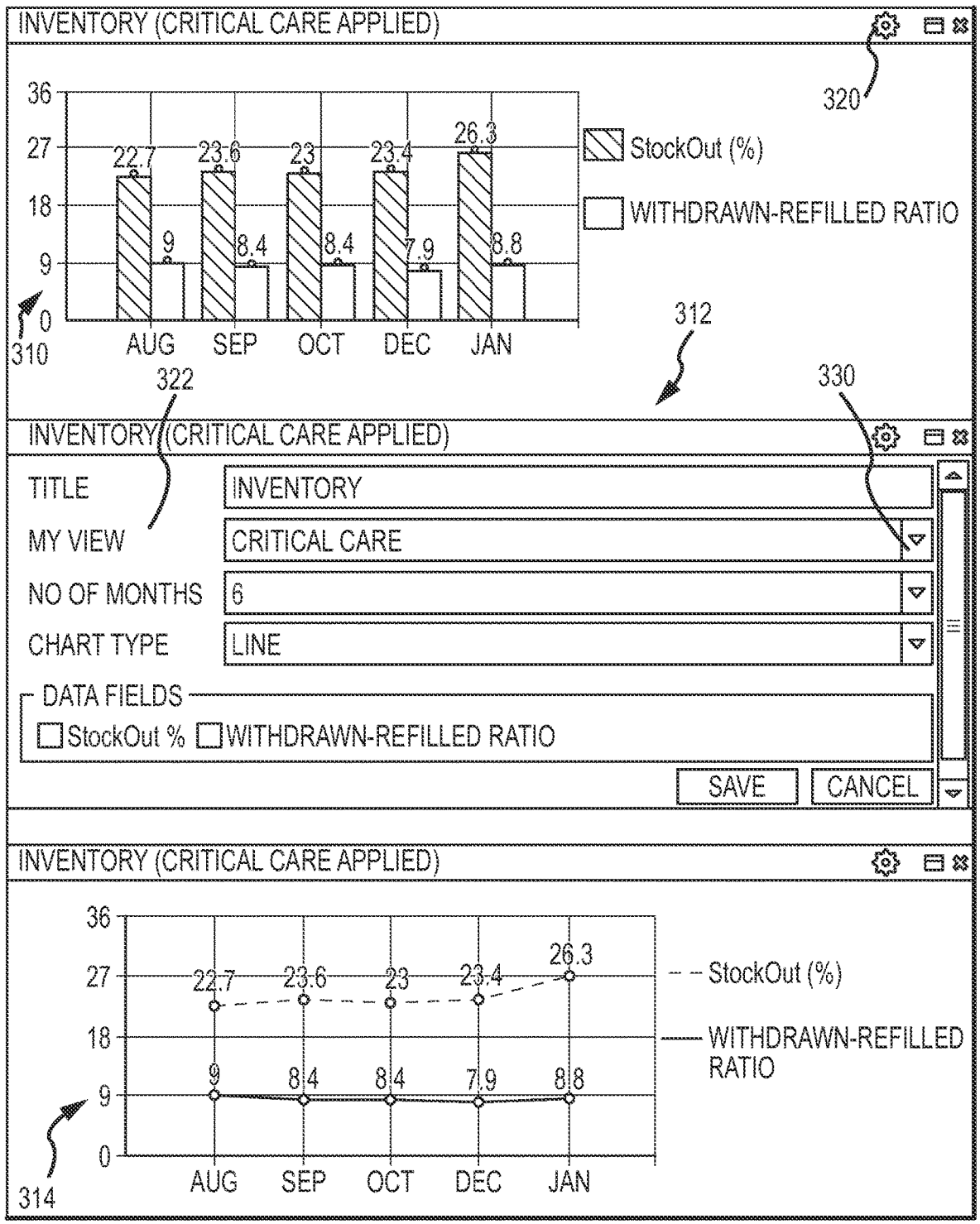
FIG. 3 is illustrates the changing of data in a widget using a selection menu.

FIG. 3 shows a widget 310, a selection menu 312 and a widget 314, for purposes of illustrating how widgets can be changed by a user to display data in different forms. The widget 310 displays vertical bars. When an icon on widget 310 (represented by "gear" 320) is selected, the selection menu 312 appears (either on the same screen as widget 310 or as a separate screen). The selection of various items at the selection menu will change widget 310 into widget 314. As illustrated, the selection for "chart type" (to display "line" data rather than bars) in menu 312 results in widget 314 appearing in place of widget 310. Thus, the user can easily change the form of the displayed data.

One feature of the selection menu 312 is the "My View" drop down bar 322. This bar is used to select the station or dispensing unit group 120 which will have data displayed. It is seen as "Critical Care" in FIG. 3. However, a drop down arrow 330 permits other groups to be displayed at drop down bar 322. A user may select any other group displayed at drop down bar 322, and in such instance, the widget 310 would be changed to widget 314, but with the indicated data for a different group displayed. As an example, assume that the user wanted to see the same data as in widget 310, but for a group that is different than Critical Care. Further assume this user has viewing rights for OR Applied. By selecting OR Applied at bar 322, the same data as in widget 310 would be displayed in widget 314, but the data would be for OR Applied rather than Critical Care.

Figure 4:
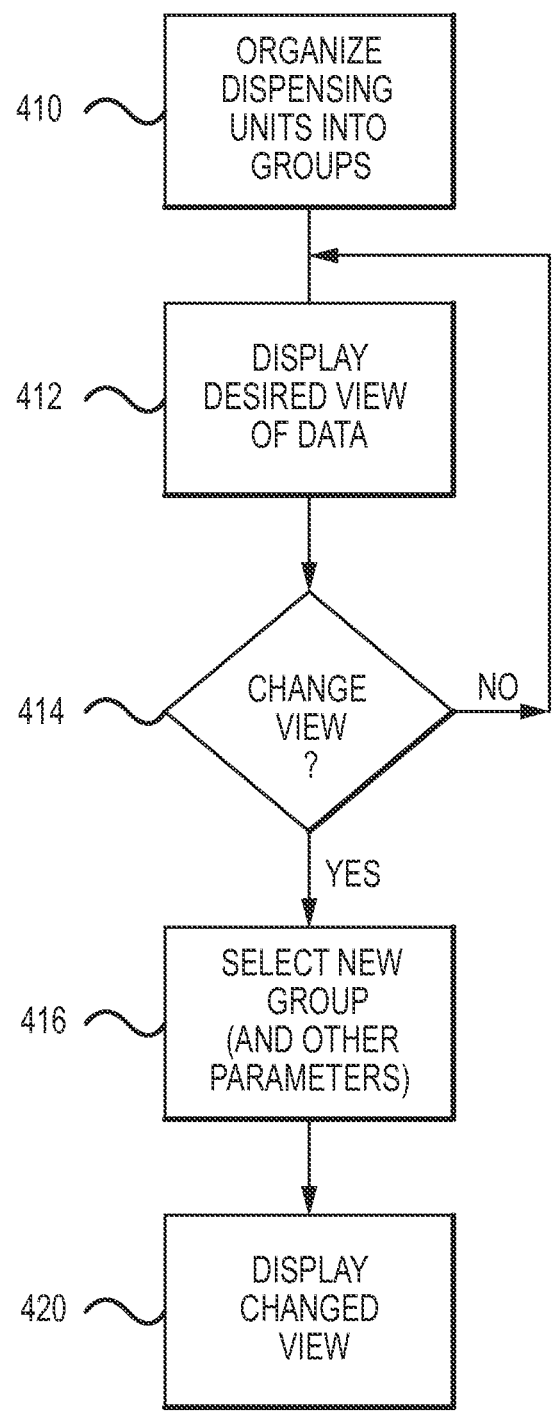
FIG. 4 is a flow diagram of a process for changing data in a widget, using the selection menu of FIG. 3.

This just mentioned feature is illustrated by the process in the flow diagram of FIG. 4. At step 410, dispensing units 110 have been organized or arranged in groups, such as illustrated in FIG. 1. At step 412, a desired widget is displayed, such as widget 310 in FIG. 3 or one of the widgets 210-224 in FIG. 2. At step 414, the user decides whether to change a widget, such as through the use of selection menu 312 seen in FIG. 3. If the widget is to be changed, then at step 416 a new dispensing unit group 120 is selected at drop down bar 322 (as should be appreciated, if no change is desired at step 414, there is no change to the displayed widget). At step 420, the changed widget is displayed (such as widget 314 in FIG. 3). As should be appreciated, the user may select changes or parameters other than the selection of a different group 120 at step 416. For example, as seen in the selection menu 312 in FIG. 3, the user may change the type of data (Title), the length of time for the display (No. of Months), and the chart type at step 416. The user may also select different kinds of data fields for display within the widget (such as the illustrated "Stock Out %" and "Withdrawn-Refilled Ratio" illustrated at selection menu 312).

In some cases, the "My View" selections at drop down bar 322 may be established in advance by the user or may be established based on responsibilities assigned to the user. While, as noted earlier, the user may want to view groups having similar levels of care, the selection could be adjusted to display similar data for two or more different groups having different levels of care, or display other combinations of data and station groups as desired by the user. Once established, the selections are thereafter easily made at the drop down bar 322.

Figure 5A:
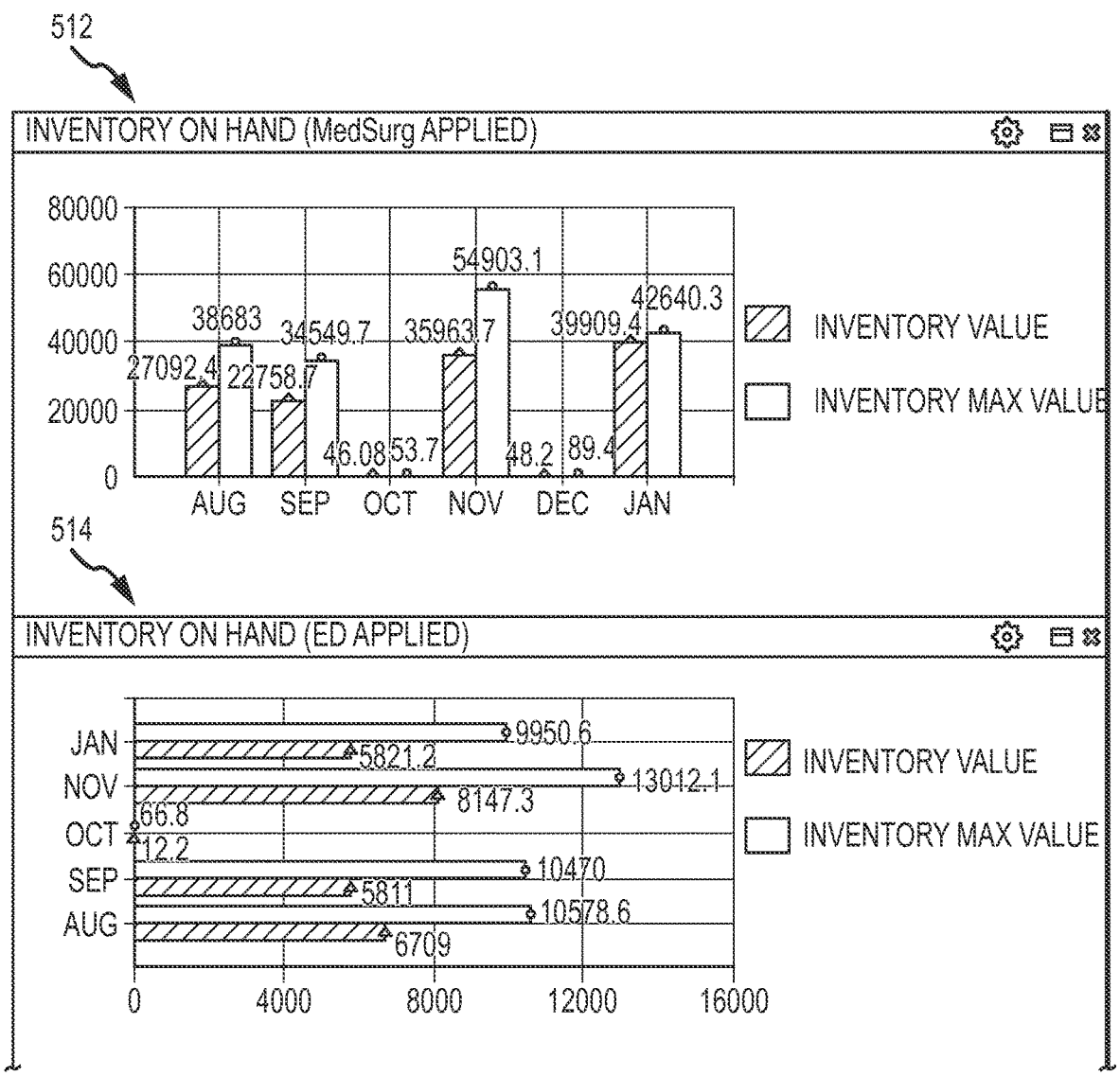

FIG. 5a illustrates two widgets 512 and 514, with widget 512 illustrating Inventory Value and Inventory Max Value (PAR Value) at the group MedSurg Applied and widget 514 illustrating Inventory Value (value on hand) and Inventory Max Value (PAR Value) at the group ED Applied, both for the months of August through January. These two widgets might be seen, among others, on a dashboard screen such as the dashboard 200 in FIG. 2. As discussed earlier, displaying inventory value (value of actual inventory in stock at dispensing units) and PAR value (desired value of inventory which will be used to replenish) can be useful in making decisions to adjust the cost of inventory.

The use of widgets (such as 512 and 514) permit a user to drill down to more detailed information associated with a group of dispensing units. For example, if a user sees a considerable difference between actual inventory value and PAR value, but also determines that actual values are fairly stable and not giving rise to "stock outs," the user may want to look at the particular dispensing units within a group to see how they are individually performing. This can be done by clicking on a bar associated with the month in question. FIG. 5b illustrates a "Cabinet Watch List" 520 that is displayed for the user (on the same screen as widgets 512 and 514) by clicking on a bar associated with the month of August, with each dispensing unit in the group displayed along with the Value on Hand and the Value at Max (PAR value). In one example, a user may choose to look at those units that have the highest Max or PAR value, since those are units that will have the highest carrying costs. If an inventory manager is asked to reduce carrying costs, the manager can look at cabinet watch list 520 and considering reducing the Max or PAR value for those cabinets that have the highest PAR values, and perhaps later monitor the dispensing unit group from time to time to make sure there has not been an unacceptable increase in stock outs. As another example, when a user sees very high actual inventory values for a group (say, higher than PAR value), this may indicate that cabinets are being overstocked (or under-utilized), and the user can drill down to the cabinet watch list to see which cabinets are in fact being replenished too often or with too much inventory (or being under-utilized), and take appropriate action.

Figure 6:
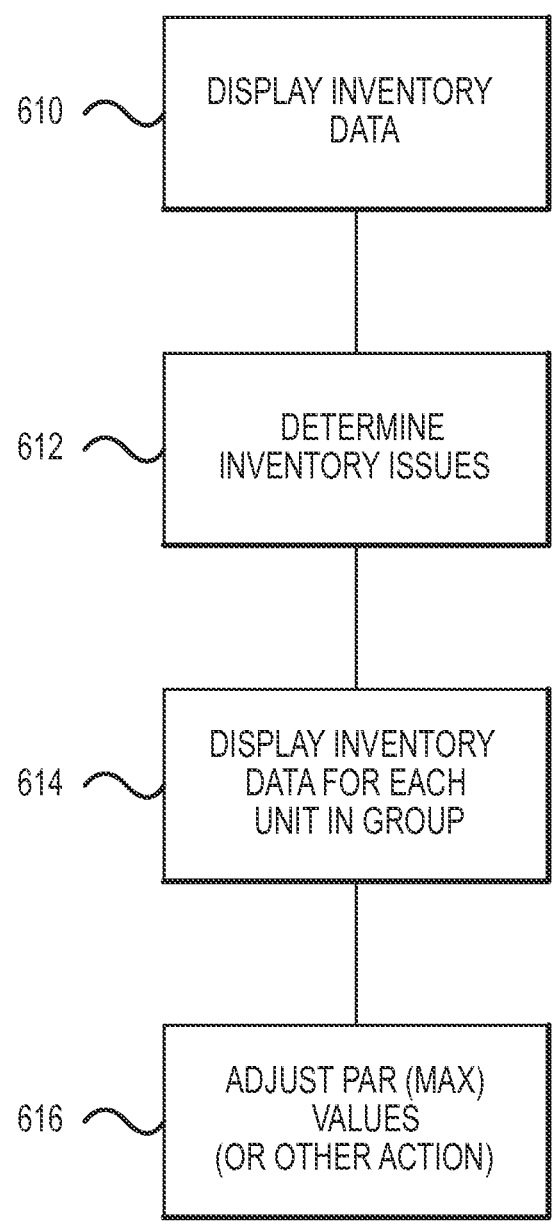
FIG. 6 is a flow diagram of a process for using the cabinet list of FIG. 5 to take action relative to inventory stored at the dispensing stations.

This general process is illustrated by the flow diagram in FIG. 6. As seen, at step 610 the user first displays inventory data (such as data represented by widgets 512 and 514) for selected groups of dispensing units or stations. The user may determine that there are inventory issues at step 612 by viewing the data, such as very high PAR values, or very high inventory on hand values (in comparison to PAR values). At step 614, the user clicks on the widget for the month in question in order to drill down and display inventory data for each dispensing unit in the group (e.g., as would be seen at cabinet watch list 520). Based on the displayed data, the user may take action (step 616), such as reducing the Max or PAR value for individual cabinets that may be contributing to the issue at hand, or relocating cabinets in order to even out usage among the cabinets.

Figure 7:
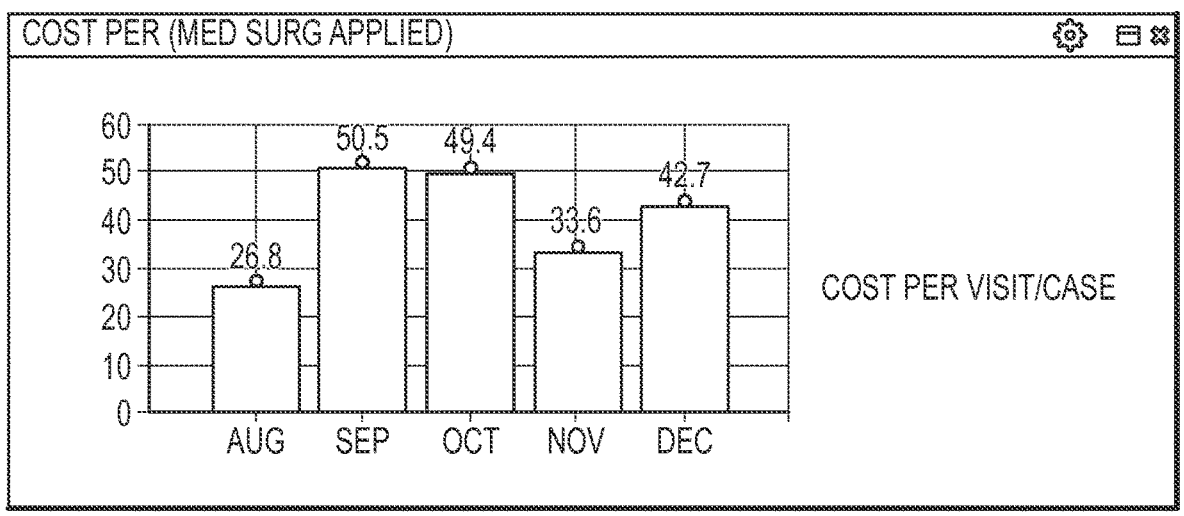
FIG. 7 illustrates a widget displaying cost per visit/case data.

FIGS. 7 and 7a illustrate the use of compliance data in conjunction with inventory data. FIG. 7 illustrates a widget 710 that displays data representing inventory data in the form of Cost Per Visit/Case (e.g., the average cost of dispensed supplies for each patient visit to a hospital) for the months of August to December for the group MedSurg Applied. A user viewing that data might take action based on inventory data changes from month to month (such as adjusting inventory in months where fewer supplies may be needed based on observed trends), but may first want to make sure the displayed data is reliable and accurate, based on compliance data that may be associated with the group for the same period of time. This was discussed earlier in conjunction with widget 212 in FIG. 2a. A widget similar to widget 212 (from FIG. 2a) could be displayed in close proximity to the widget 710 in FIG. 7 (assuming they were for the same group and the same months) and the comparison used to determine how reliable the data in widget 710 is, especially if the user intends to act on it. In some instances, the user may want to drill down further to see data underlying compliance data. This is illustrated in FIG. 7a, which is more detailed exemplary compliance information on two dispensing units or stations OCBLUE1 and OCCTSURE1, showing compliance percentages for each of those dispensing units at a list or screen 720. In this case, the compliance data is categorized for both billable items and non-billable items (items for which the hospital does not charge), but with actual compliance data shown only for billable items. As seen in FIG. 7a, the compliance percentage for one unit (OCBLUE1) for a given month is only 18.33% (i.e., in only 18.33% of the times when measured, such as at the time of audits, the data at the station is found to be accurate). For the other illustrated station (OCCTSURE1), the compliance percentage is 36%. Since 100% would indicate full compliance, a user might view the displayed inventory data (such as for the month seen in screen 720) as not reliable or accurate, and thus not take action based on the data displayed in the widget 710 for that month.

Figure 8:
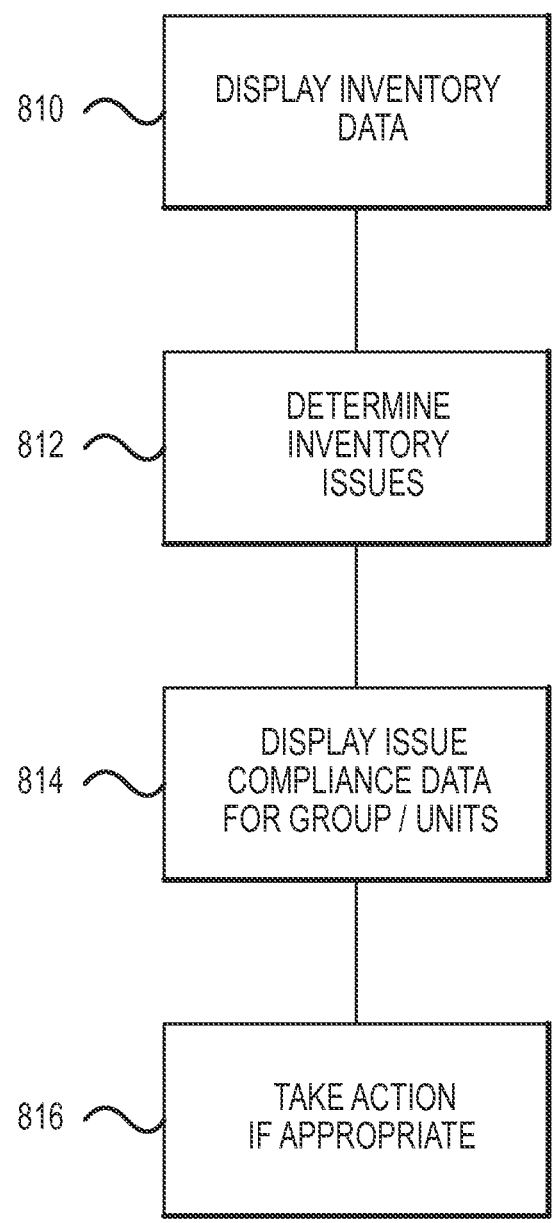
FIG. 8 is a flow diagram of a process for using the compliance list of FIG. 7 to determine the reliability of the data displayed at the widget of FIG. 7.

A process for using compliance data is illustrated by the flow diagram in FIG. 8. At step 810, inventory data (such as the exemplary data seen at widget 710 in FIG. 7) is displayed to a user. At step 812, the user may determine that there could be inventory issues based on the displayed data, but before taking action on the data, the user decides to view issue compliance data for the group in question at step 814. The compliance data could be in the form of a widget (such as widget 212). The user might also choose to drill down to see compliance data for individual cabinets within the group, such as that seen in the list 720 in FIG. 7a. In one embodiment, displaying list 720 might result from clicking on a bar or graph (e.g., for a given month) within a widget displaying compliance data (such as widget 212 seen in FIG. 2a). After viewing the compliance data, the user may take action (if appropriate, given the compliance data), at step 816. In some instances, appropriate action might involve training the care providers using the cabinets in question, to improve workflow procedures (e.g., consistently entering data at the time items are withdrawn). As mentioned earlier, the degree of compliance expected might depend on the level of care provided, with lower compliance expected (and tolerated) at higher care locations.

As mentioned earlier, the reported inventory data may be processed using various statistical techniques to identify issues arising from data collected at the user system 140. One such technique is illustrated in FIGS. 9, 10 and 11.

Figure 9:
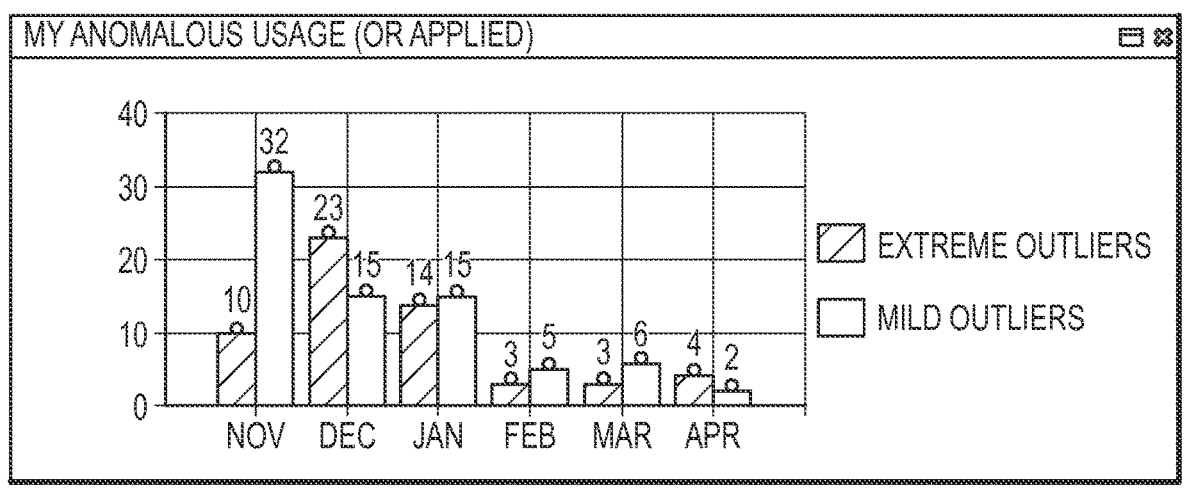
FIG. 9 illustrates a graphical view displaying "outliners" in use of supplies at a group of dispensing stations, to identify possible diversion of supplies.

In FIG. 9, a widget 910 is displayed for anomalous usage at the station group "OR Applied." This particular display shows dispensing activities (outliers) that are outside a normal range of activity, with the outliers being identified as either "mild" or "extreme." In the particular widget 910, the anomalous data relates to withdrawals of narcotic items from dispensing stations in the identified group "OR Applied". The widget displays withdrawals by users for each of six months (November through April), which have been statistically identified as either mild outliers or extreme outliers. Mild outliers represent relatively high rates of withdrawal which might be explained in certain circumstances (for example, an increase in patients having conditions requiring pain medication). Extreme outliers represent extremely high rates of withdrawals which might be more difficult to explain.

The identification of outliers is done using the statistical technique referred to as "box plots" (or "box and whisker plots"), which will be explained in conjunction with FIG. 10. General box plot analysis is described in "Box and Whisker Plots," published by The Math Forum at Drexel University (2000), http://mathforum.org/library/drmath/view/52188.html, and "How to Interpret a Box Plot in Terms of a Normal Distribution," published by McMaster University (1999), http://www.math.mcmaster.ca/peter/s2ma3/s2ma3_9798/boxplots.html, both of which are hereby incorporated by reference.

Figure 10:
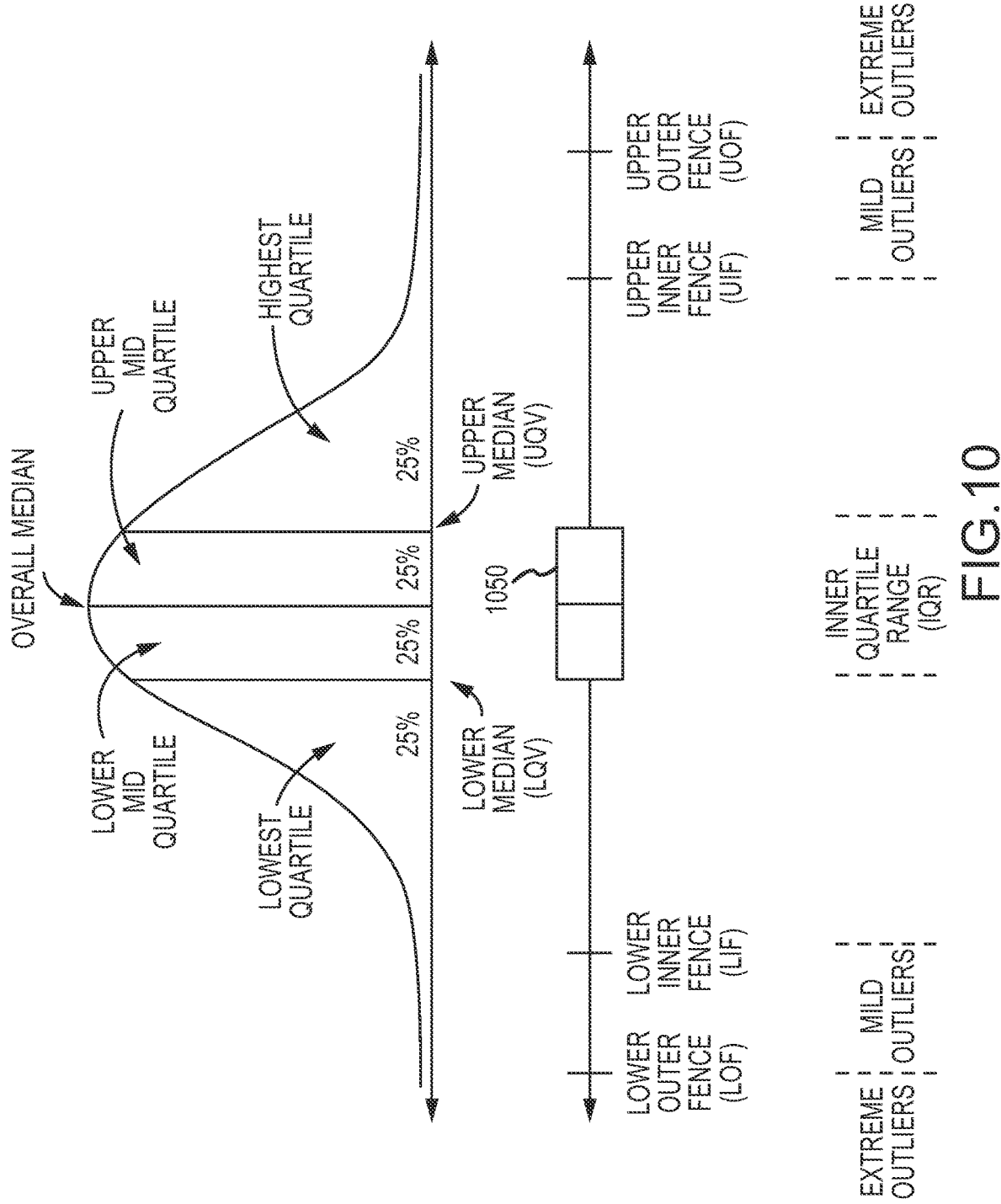
FIG. 10 is a graph illustrating a "box plot" method of statistical analysis for identifying outliers.

In FIG. 10, there is illustrated an exemplary graph having a normal "bell shaped" distribution of data (and thus assumes a somewhat uniform distribution of data). The underlying data would represent the number of units of a narcotic that have been withdrawn from an identified station group by each user in a population of users of the dispensing stations in that group. The data on the graph is arranged in quartiles, with 50% of the users (the two lower quartiles) having fewer withdrawals than the median (the overall median for the entire data set) and 50% (the two upper quartiles) having a more withdrawals than the overall median. It should be appreciated that in actual practice (especially for a smaller population, such users at dispensing stations), the data might not be as uniform, and the data curve might be not as uniform about the median.

In the "box and whisker" technique, a box 1050 is defined to include the first quartile above the median (upper mid quartile) and the first quartile below the median (lower mid quartile). The lower end of the box LQV ("lower quartile value", sometimes also referred to as the "lower hinge") represents a value (e.g., number of withdrawals) for the user represented at the point between the lowest quartile and the lower mid quartile, and the upper end of the box UQV ("upper quartile value," sometimes also referred to as the "upper hinge") represents a value (e.g., number of withdrawals) for the user represented at the point between the highest quartile and the upper mid quartile.

A Lower Outer Fence (LOF), Lower Inner Fence (LIF), Upper Inner Fence (UIF), and Upper Outer Fence (UOF) for the data are calculated and used to define mild outliers and extreme outliers. In particular, users that fall between the UIF and UOF are mild outliers, and users that fall outside or beyond the UOF are extreme outliers. For purposes of identifying outliers at dispensing stations in this embodiment, it is assumed that users who fall below the overall median (users that access fewer narcotic items) are not of interest, but users that fall above the overall median are of potential interest. So, for purposes of reporting (e.g., FIG. 9), the mild outliers and extreme outliers identified are only those found in relation to the upper fences (UIF and UOF). It will be appreciated, of course, that in the analysis of other inventory data, mild outliers and extreme outliers found in relation to the lower fences (LIF and LOF) might be of interest.

The upper inner fence and upper outer fence are computed using the following formula:

$$UIF = 1.5 \times IQR$$

$$UOF = 3.0 \times IQR,$$

where IQR (inner quartile range) represents the difference between UQV and LQV (UQV being the upper median data value at the point between the highest quartile and the upper mid quartile, and LQV being the lower median data value at the point between the lowest quartile and the lower mid quartile).

In the embodiment illustrated in FIG. 9, a box plot analysis is done for each of the different narcotics dispensed at the dispensing units, in order to determine outliers for each narcotic.

As an example, for the station group "OR Applied" which has data displayed in FIG. 9, assume that the user system 140 tracks, for a given month, the number of each narcotic dispensed to each of the personnel having access to the dispensing units in that group. For one given narcotic, assume further that there are 25 people using the units in the dispensing group, the median number of items withdrawn for the narcotic is 4, the UQV is 15 and the LQV is 7. Thus, in this example:

IQR is 8
UIF is 12
UOF is 24.

Thus, for the specific narcotic and for the given month, a mild outlier would be any person (in the group of 25 users) having dispensed between 12 and 24 items (between UIF and UOF), and extreme outliers would be any person having more than 24 items dispensed (beyond UOF).

The same box plot analysis is done of each of the other narcotics stored at the dispensing units for the same month, and the number of outliers (for all the different narcotics) would give rise to the graphical view shown in FIG. 9 (when collected over several months).

Referring to FIG. 9, for the month of November, 10 extreme outliers and 32 mild outliers have been identified for all the tracked narcotics at dispensing units in station group OR Applied. It should be appreciated that a person having items dispensed could be mild outlier for one narcotic, an extreme outlier for another narcotic, and not an outlier for a third narcotic. Thus, it would be desirable for a user to drill down deeper into the data seen in FIG. 9.

This could be done by clicking on the given month displayed in FIG. 9, which would give rise to details of users (and their withdrawals) that are identified as outliers in FIG. 9. The result would be a report as seen in FIG. 11, where there is displayed both (1) each user identified as having withdrawals giving rise to statistical outliers, and (2) the number of extreme and mild outliers associated with that user. In FIG. 11, it can be seen that one user ("Evander McCrae") has, in November, two extreme outliers (for narcotic withdrawals) and three mild outliers (for narcotics withdrawals). This particular user could be a cause of concern to the person monitoring inventory at the dispensing units. Further details could be obtained by clicking on the name of the user appearing in FIG. 11, to get the specifics of each outlier situation for that user (e.g., the type of narcotic that gave rise to the statistical outlier). Appropriate follow-up action could be taken. For example, an inventory manager could interview the user in question if necessary to better assess whether improper diversion of the narcotics has occurred.

Figure 12:
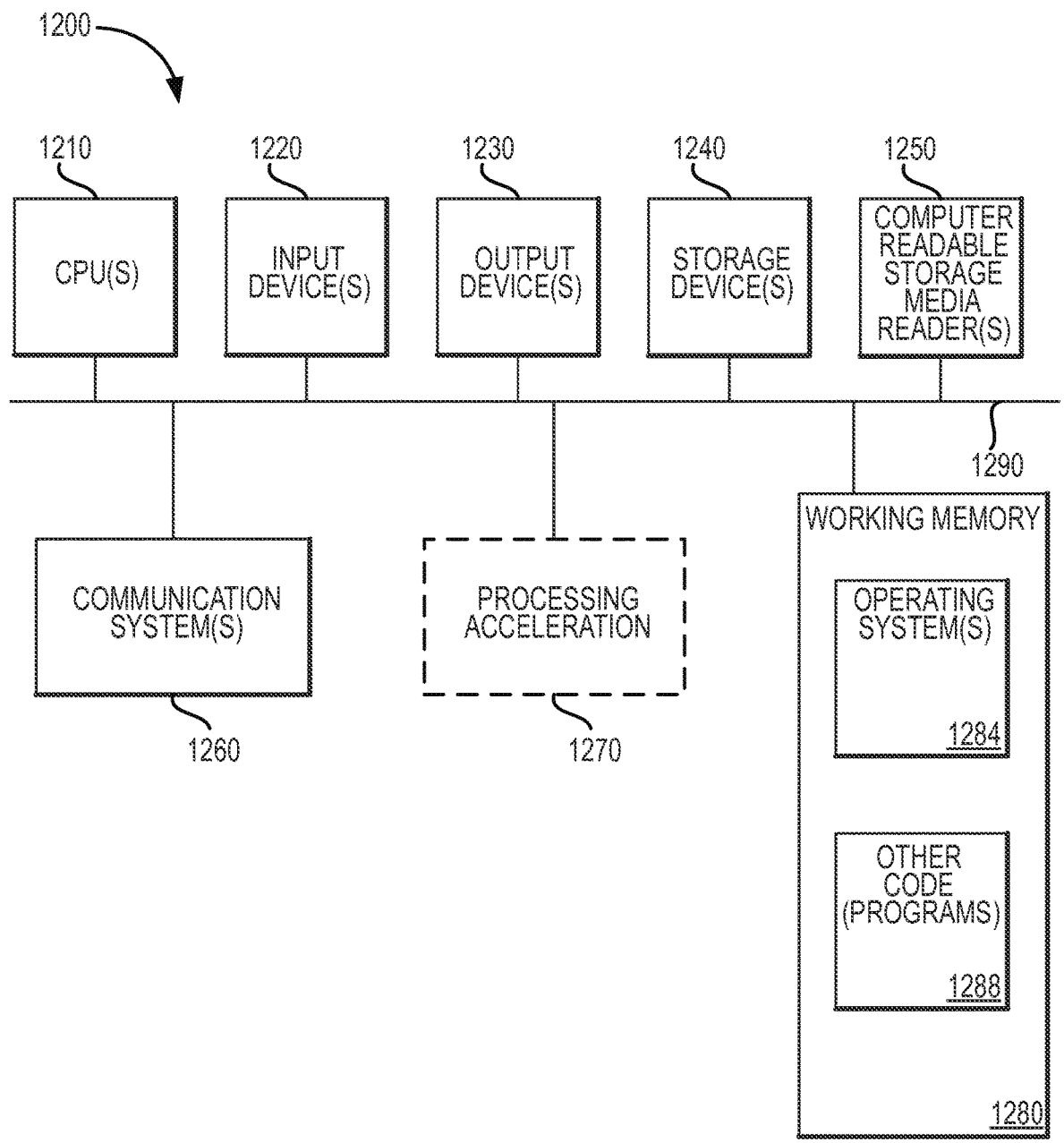
FIG. 12 is a block diagram illustrating an exemplary computer system upon which embodiments of the present invention may be implemented

FIG. 12 is a block diagram illustrating an exemplary computer system upon which embodiments of the present invention may be implemented. This example illustrates a computer system 1200 such as may be used, in whole, in part, or with various modifications, to provide the functions of the system at dispensing units 110, the central server 130, and the user system 140, as well as other components and functions of the invention described herein.

The computer system 1200 is shown comprising hardware elements that may be electrically coupled via a bus 1290. The hardware elements may include one or more central processing units 1210, one or more input devices 1220 (e.g., a mouse, a keyboard, scanner, etc.), and one or more output devices 1230 (e.g., a display device, a printer, etc.). The computer system 1200 may also include one or more storage devices 1240, representing remote, local, fixed, and/or removable storage devices and storage media for temporarily and/or more permanently containing computer-readable information, and one or more storage media reader(s) 1250 for accessing the storage device(s) 1240. By way of example, storage device(s) 1240 may be disk drives, optical storage devices, solid-state storage device such as a random access memory ("RAM") and/or a read-only memory ("ROM"), which can be programmable, flash-updateable or the like.

The computer system 1200 may additionally include a communications system 1260 (e.g., a modem, a network card—wireless or wired, an infra-red communication device, a Bluetooth™ device, a near field communications (NFC) device, a cellular communication device, etc.) The communications system 1260 may permit data to be exchanged with a network, system, computer, mobile device and/or other component as described earlier. The system 1200 also includes working memory 1280, which may include RAM and ROM devices as described above. In some embodiments, the computer system 1200 may also include a processing acceleration unit 1270, which can include a digital signal processor, a special-purpose processor and/or the like.

The computer system 1200 may also comprise software elements, shown as being located within a working memory 1280, including an operating system 1284 and/or other code 1288. Software code 1288 may be used for implementing functions of various elements of the architecture as described herein. For example, software stored on and/or executed by a computer system, such as system 1200, can be used in implementing the processes seen in FIGS. 4, 6 and 8.

It should be appreciated that alternative embodiments of a computer system 1200 may have numerous variations from that described above. For example, customized hardware might also be used and/or particular elements might be implemented in hardware, software (including portable software, such as applets), or both. Furthermore, there may be connection to other computing devices such as network input/output and data acquisition devices (not shown).

While various methods and processes described herein may be described with respect to particular structural and/or functional components for ease of description, methods of the invention are not limited to any particular structural and/or functional architecture but instead can be implemented on any suitable hardware, firmware, and/or software configuration. Similarly, while various functionalities are ascribed to certain individual system components, unless the context dictates otherwise, this functionality can be distributed or combined among various other system components in accordance with different embodiments of the invention. As one example, the system at dispensing units 110, the central server 130 and the user system 140 may each be implemented by a single system having one or more storage device and processing elements. As another example, the units 110, central server 130 and user system 140 may each be implemented by plural systems, with their respective functions distributed across different systems either in one location or across a plurality of linked locations.

Moreover, while the various flows and processes described herein (e.g., those illustrated in FIGS. 4, 6 and 8) are described in a particular order for ease of description, unless the context dictates otherwise, various procedures may be reordered, added, and/or omitted in accordance with various embodiments of the invention. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments may be described with (or without) certain features for ease of description and to illustrate exemplary features, the various components and/or features described herein with respect to a particular embodiment can be substituted, added, and/or subtracted to provide other embodiments, unless the context dictates otherwise. Further, the term "exemplary" used herein does not mean that the described example is preferred or better than other examples. Consequently, although the invention has been described with respect to exemplary embodiments, it will be appreciated that the invention is intended to cover all modifications and equivalents within the scope of the following claims and other claims that may be supported by the descriptions herein.

What is claimed is:

1. A dispensing system, comprising:
a plurality of dispensing stations, each station having a plurality of storage locations for storing items to be dispensed, wherein the dispensing stations are arranged in a plurality of station groups, and wherein each of the station groups includes more than one of the dispensing stations;
a database for storing inventory data collected over time and relating to the items stored, at the dispensing stations; and
a processor programmed to execute a sequence of instructions to cause the processor to display, at a display device, inventory data for a user, by:
receiving from the user a first station group identifier identifying a first station group for which inventory data is to be displayed;
receiving from the user a second station group identifier identifying a second station group for which inventory data is to be displayed;
receiving from the user, a time identifier identifying a period of time for which the inventory data is to be displayed;
calculating statistical outliers from the inventory data for at least one of the identified station groups for the identified period of time, wherein the outliers reflect anomalous usage at the one identified station group outside a normal range of activity; and
displaying simultaneously, at the display device, at least two graphic views of data relating to inventory for both the first identified station group and the second identified station group, for the identified period of time, including, at least the statistical outliers, with the graphic views displayed side-by-side.

2. The system of claim 1, wherein the statistical outliers comprise either mild outliers or extreme outliers.

3. The system of claim 1, wherein the stored inventory data comprises data pertaining to accessing items at a dispensing station, including data identifying the items accessed, identifying the dispensing station of the items accessed, and identifying the time of access.

4. The system of claim 1, wherein the inventory data relates to inventory on hand at the identified station group.

5. The system of claim 4, wherein the inventory on hand at the identified station group is measured by the cost of such inventory.

6. The system of claim 1, wherein the inventory data relates to stock-outs at the identified station group, the stock-outs reflecting instances in which a dispensing station is accessed for an item that is out of stock.

7. The system of claim 1, wherein the inventory data relates to withdrawn-refilled ratios at the identified station group, the withdrawn-refilled ratios reflecting how often items are dispensed in relation to how often the same items are replenished.

8. The system of claim 1, wherein the inventory data relates to compliance data at the identified station group, the compliance data reflecting instances in which a dispensing station is accessed for an item, but such dispensing of the item was cancelled.

9. The system of claim 1, wherein the inventory data relates to compliance data at the identified station group, the compliance data reflecting any discrepancy between (1) a reported number of items reported as dispensed to users accessing a dispensing station and (2) an actual number of items dispensed to users accessing the dispensing station as indicated in an audit of the dispensing station.

10. The system of claim 1, wherein the inventory data relates to compliance data at the identified station group, the compliance data reflecting access to a dispensing station, but no report by the user of an item being removed during that access.

11. The system of claim 1, wherein the inventory data relates to the dispensing of addictive items.

12. The system of claim 1, wherein the statistical outliers comprise either mild outliers or extreme outliers and wherein the processor is further programmed to execute a sequence of instructions to cause the processor to:
determine an inner data fence (IF) and an outer data fence (OF) of data values, wherein mild outliers are data values located between the inner data fence and the outer data fence and extreme outliers are data values located beyond the outer data fence, wherein the inner data fence and outer data fence are determine by the equation:

$$IF=1.5\times IQR;$$

$$OF=3.0\times IQR;$$

wherein $IQR=UQV-IQV$;
wherein the data values in the inventory data are arranged in quartiles according to value, including a lowest data quartile, a lower mid data quartile, an upper mid data quartile, and a highest data quartile;
wherein the lowest data quartile has the lowest quartile of data values, the lower mid data quartile has a quartile of data values between the lowest data quartile and the median of all data values, the upper mid data quartile has a quartile of data values between the median of all data values and the highest data quartile, and the highest quartile has the highest quartile of data values;
wherein UQV is an upper median data value between the highest data quartile and the upper mid data quartile; and
wherein LQV is a lower median data value between the lowest data quartile and the lower mid data quartile.

13. In a dispensing system comprising a plurality of dispensing stations, each station having a plurality of storage locations for storing items to be dispensed, wherein the dispensing stations are arranged in a plurality of station groups, and wherein each of the plurality of station groups includes more than one of the dispensing stations, a method of displaying inventory data, the method comprising:
storing, at a database, inventory data collected over time and relating to the items stored at the dispensing stations;
receiving, by one or more processors, a first station group identifier identifying a first station group for which inventory data is to be displayed;
receiving, by one or more processors, a second station group identifier identifying a second station group for which inventory data is to be displayed;
receiving, by one or more of the processors, a time identifier identifying a period of time for which the inventory data is to be, displayed;
calculating statistical outliers from the inventory data for at least one of the identified station groups for the identified period of time, wherein the outliers reflect anomalous usage at the one identified station group outside a normal range of activity; and displaying, at a display device, at least two graphic views of data relating to inventory for the first identified station group and the second identified station group, for the identified period of time, including at least the statistical outliers, with the graphic views displayed side-by-side.

14. The method of claim 13, wherein the statistical outliers comprise either mild outliers or extreme outliers.

15. The method of claim 13, wherein the stored inventory data comprises data pertaining to accessing items at a dispensing station, including data identifying the items accessed, identifying the dispensing station of the items accessed, and identifying the time of access.

16. The method of claim 13, wherein the inventory data relates to inventory on hand at the identified station group.

17. The method of claim 16, wherein the inventory on hand at the identified station group is measured by the cost of such inventory.

18. The method of claim 13, wherein the inventory data relates to stock-outs at the identified station group, the stock-outs reflecting instances in which a dispensing station is accessed for an item that is out of stock.

19. The method of claim 13, wherein the inventory data relates to withdrawn-refilled ratios at the identified station group, the withdrawn-refilled ratios reflecting how often items are dispensed in relation to how often the same items are replenished.

20. The method of claim 13, wherein the inventory data relates to compliance data at the identified station group, the compliance data reflecting instances in which a dispensing station is accessed for an item, but such dispensing of the item was cancelled.

21. The method of claim 13, wherein the inventory data relates to compliance data at the identified station group, the compliance data reflecting any discrepancy between (1) a reported number of items reported as dispensed to users accessing a dispensing station and (2) an actual number of items dispensed to users accessing the dispensing station as indicated in an audit of the dispensing station.

22. The method of claim 13, wherein the inventory data relates to compliance data at the identified station group, the compliance data reflecting access to a dispensing station, but no report by the user of an item being removed during that access.

23. The system of claim 13, wherein the inventory data relates to the dispensing of addictive items.

24. The method of claim 13, wherein the statistical outliers comprise either mild outliers or extreme outliers and wherein the processor is further programmed to execute a sequence of instructions to cause the processor to:

determine an inner data fence (IF) and an outer data fence (OF) of data values, wherein mild outliers are data values located between the inner data fence and the outer data fence and extreme outliers are data values located beyond the outer data fence, wherein the inner data fence and outer data fence are determine by the equation:

$$IF=1.5\times IQR;$$

$$OF=3.0\times IQR;$$

wherein IQR=UQV−IQV;

Wherein the data values in the inventory data are arranged in quartiles according to value, including a lowest data quartile, a lower mid data quartile, an upper mid data quartile, and a highest data quartile;

wherein the lowest data quartile has the lowest quartile of data values, the lower mid data quartile has a quartile of data values between the lowest data quartile and the median of all data values, the upper mid data quartile has a quartile of data values between the median of all data values and the highest data quartile, and the highest quartile has the highest quartile of data values;

wherein UQV is an upper median data value between the highest data quartile and the upper mid data quartile; and wherein LQV is a lower median data value between the lowest data quartile and the lower mid data quartile.

25. The system of claim 1, wherein the first identified station group and the second identified station group are different.

* * * * *

UNITED STATES PATENT AND TRADEMARK OFFICE
CERTIFICATE OF CORRECTION

PATENT NO. : 10,586,022 B2
APPLICATION NO. : 14/084967
DATED : March 10, 2020
INVENTOR(S) : Jason Czaplewski et al.

It is certified that error appears in the above-identified patent and that said Letters Patent is hereby corrected as shown below:

In the Specification

Column 3, Line 3:
Delete "implemented" and insert -- implemented. --, therefor.

Column 10, Line 2 and Line 3:
Delete the extra spaces which are causing the phrase "Cabinet Watch List" to be separated and make Lines 1 to 23, one continuous paragraph.

In the Claims

Claim 6, Column 15, Line 53:
Delete "Stock-outs" and insert -- stock outs --, therefor.

Claim 17, Column 17, Line 23:
Delete "Stock-outs" and insert -- stock outs --, therefor.

Claim 23, Column 18, Line 6:
Delete "system" and insert -- methods --, therefor.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*